(12) United States Patent
Viola et al.

(10) Patent No.: US 7,461,767 B2
(45) Date of Patent: Dec. 9, 2008

(54) BATTERY POWERED SURGICAL INSTRUMENT

(75) Inventors: Frank J. Viola, Sandy Hook, CT (US); Gregg Krehel, Newtown, CT (US); Guido Pedros, Shelton, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 65 days.

(21) Appl. No.: 11/446,283

(22) Filed: Jun. 2, 2006

(65) Prior Publication Data

US 2006/0278681 A1 Dec. 14, 2006

Related U.S. Application Data

(60) Provisional application No. 60/687,406, filed on Jun. 3, 2005, provisional application No. 60/687,244, filed on Jun. 3, 2005.

(51) Int. Cl.
*A61B 17/068* (2006.01)
(52) U.S. Cl. ............... 227/175.2; 227/19; 227/176.1; 606/139; 606/219
(58) Field of Classification Search ............ 227/19, 227/176.1, 175.2, 175.1, 180.1; 606/219, 606/139, 9, 127, 143, 151; 173/20
See application file for complete search history.

(56) References Cited

U.S. PATENT DOCUMENTS

| | | |
|---|---|---|
| 4,508,253 A | 4/1985 | Green |
| 4,508,523 A | 4/1985 | Leu |
| 4,606,344 A | 8/1986 | Di Giovanni |
| 4,990,153 A | 2/1991 | Richards |
| 5,300,081 A | 4/1994 | Young et al. |
| 5,364,001 A | 11/1994 | Bryan |
| 5,383,880 A | 1/1995 | Hooven |
| 5,389,098 A | 2/1995 | Tsuruta et al. |
| 5,395,033 A | 3/1995 | Byrne et al. |
| 5,403,312 A | 4/1995 | Yates et al. |
| 5,411,508 A | 5/1995 | Bessler et al. |

(Continued)

FOREIGN PATENT DOCUMENTS

EP 0 537 570 B1 4/1993

(Continued)

OTHER PUBLICATIONS

Detemple, P., "Microtechnology in Modern Health Care", *Med Device Technol.* 9(9):18-25 (1998).

*Primary Examiner*—Scott A. Smith (57) ABSTRACT

A surgical stapler has a handle assembly including a stationary handle and a trigger. The stapler also has a drive assembly with a body having a working end and a cam member supported on the working end. The cam member is positioned to translate relative to the anvil to maintain the anvil in the closed position during firing of the stapler. The trigger is operatively connected to a power cell. The power cell is operably connected to a motor of the drive assembly. The manipulation of the trigger actuates the power cell such that the power cell powers the drive assembly to effect translation of the cam member relative to the anvil. The stapler also has a channel for supporting the staple cartridge and the motor of the drive assembly controls the actuation sled supported within the cartridge. The actuation sled urges the plurality of staples from the cartridge when the anvil is in the closed position and in cooperative alignment with the staple cartridge.

11 Claims, 10 Drawing Sheets

U.S. PATENT DOCUMENTS

| | | | |
|---|---|---|---|
| 5,464,144 A | 11/1995 | Guy et al. |
| 5,478,344 A | 12/1995 | Stone et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,937 A | 7/1996 | Boiarski et al. |
| 5,558,671 A | 9/1996 | Yates |
| 5,562,239 A | 10/1996 | Boiarski et al. |
| 5,582,611 A | 12/1996 | Tsuruta et al. |
| 5,624,452 A | 4/1997 | Yates |
| 5,658,300 A | 8/1997 | Bito et al. |
| 5,665,085 A | 9/1997 | Nardella |
| 5,667,517 A | 9/1997 | Hooven |
| 5,695,524 A | 12/1997 | Kelley et al. |
| 5,713,896 A | 2/1998 | Nardella |
| 5,715,987 A | 2/1998 | Kelley et al. |
| 5,716,366 A | 2/1998 | Yates |
| 5,735,848 A | 4/1998 | Yates et al. |
| 5,782,397 A | 7/1998 | Koukline |
| 5,810,811 A | 9/1998 | Yates et al. |
| 5,849,028 A | 12/1998 | Chen |
| 5,861,005 A | 1/1999 | Kontos |
| 5,876,401 A | 3/1999 | Schulze et al. |
| 5,918,791 A | 7/1999 | Sorrentino et al. |
| 5,928,222 A | 7/1999 | Kleinerman |
| 5,944,717 A | 8/1999 | Lee et al. |
| 5,954,259 A | 9/1999 | Viola et al. |
| 5,964,394 A | 10/1999 | Robertson |
| 5,980,518 A | 11/1999 | Carr et al. |
| 5,980,548 A | 11/1999 | Evans et al. |
| 5,991,650 A | 11/1999 | Swanson et al. |
| 6,004,335 A | 12/1999 | Vaitekunas et al. |
| 6,007,550 A | 12/1999 | Wang et al. |
| 6,010,054 A * | 1/2000 | Johnson et al. | 227/176.1 |
| 6,032,849 A | 3/2000 | Mastri et al. |
| 6,039,731 A | 3/2000 | Taylor et al. |
| 6,063,078 A | 5/2000 | Wittkampf |
| 6,063,095 A | 5/2000 | Wang et al. |
| 6,080,150 A | 6/2000 | Gough |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A * | 10/2000 | Mayer | 606/1 |
| 6,127,811 A | 10/2000 | Shenoy et al. |
| 6,132,425 A | 10/2000 | Gough |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,293,943 B1 | 9/2001 | Panescu et al. |
| 6,315,184 B1 | 11/2001 | Whitman |
| 6,330,965 B1 | 12/2001 | Milliman et al. |
| 6,346,104 B2 | 2/2002 | Daly et al. |
| H2037 H | 7/2002 | Yates et al. |
| 6,412,279 B1 | 7/2002 | Coleman et al. |
| 6,436,097 B1 | 8/2002 | Nardella |
| 6,436,107 B1 | 8/2002 | Wang et al. |
| 6,443,973 B1 | 9/2002 | Whitman |
| 6,478,210 B2 | 11/2002 | Adams et al. |
| 6,505,768 B2 | 1/2003 | Whitman |
| 6,601,749 B2 | 8/2003 | Sullivan et al. |
| 6,602,252 B2 | 8/2003 | Mollenauer |
| 6,616,821 B2 | 9/2003 | Broadley et al. |
| 6,656,177 B2 | 12/2003 | Truckai et al. |
| 6,669,705 B2 | 12/2003 | Westhaver et al. |
| 6,696,008 B2 | 2/2004 | Brandinger |
| 6,698,643 B2 | 3/2004 | Whitman |
| 6,716,233 B1 | 4/2004 | Whitman |
| 6,817,508 B1 | 11/2004 | Racenet et al. |
| 6,830,174 B2 * | 12/2004 | Hillstead et al. | 227/175.1 |
| 6,843,403 B2 | 1/2005 | Whitman |
| 6,872,214 B2 | 3/2005 | Sonnenschein et al. |
| 6,900,004 B2 | 5/2005 | Satake |
| 6,905,057 B2 * | 6/2005 | Swayze et al. | 227/176.1 |
| 6,926,636 B2 | 8/2005 | Luper |
| 6,981,941 B2 | 1/2006 | Whitman et al. |
| 6,988,649 B2 * | 1/2006 | Shelton et al. | 227/175.2 |
| 7,032,798 B2 * | 4/2006 | Whitman et al. | 227/175.1 |
| 7,044,353 B2 | 5/2006 | Mastri et al. |
| 7,059,508 B2 * | 6/2006 | Shelton et al. | 227/175.2 |
| 7,077,856 B2 | 7/2006 | Whitman |
| 7,122,029 B2 * | 10/2006 | Koop et al. | 606/9 |
| 7,140,528 B2 | 11/2006 | Shelton, IV |
| 7,246,734 B2 * | 7/2007 | Shelton, IV | 227/175.1 |
| 2002/0165541 A1 | 11/2002 | Whitman |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0145674 A1 | 7/2005 | Sonnenschein et al. |
| 2006/0097025 A1 | 5/2006 | Milliman et al. |

FOREIGN PATENT DOCUMENTS

| | | |
|---|---|---|
| EP | 0 647 431 A2 | 4/1995 |
| EP | 0 738 501 A1 | 10/1996 |
| WO | WO 97/40760 A1 | 11/1997 |
| WO | WO 99/52489 A1 | 10/1999 |

* cited by examiner

BATTERY POWERED SURGICAL INSTRUMENT

CROSS REFERENCE TO RELATED PATENT APPLICATIONS

This patent application claims priority to U.S. Provisional Patent Application Ser. No. 60/687,406 to Viola, et al., filed on Jun. 3, 2005 which is herein incorporated by reference in its entirety. This patent application also claims priority to U.S. Provisional Patent Application Ser. No. 60/687,244 to Viola, et al., filed on Jun. 3, 2005 which is also herein incorporated by reference in its entirety. This patent application also relates to U.S. patent application Ser. No. 11/446,282 to Viola, et al., filed contemporaneously with the instant patent application which is herein incorporated by reference in its entirety.

BACKGROUND

1. Technical Field

The present disclosure relates to surgical instruments. More particularly, the present disclosure relates to a surgical stapling device that has an improved and internally powered driving mechanism.

2. Background of the Related Art

Surgeons have recognized in the art the benefits of a compact surgical apparatus for the application of surgical clips and staples to body tissue in a number of different medical procedures. Often, prior art surgical staplers require some degree of physical force or lateral movement in order to operate a handle to actuate the surgical stapler and fire the staple after a compression to actuate the surgical stapler and fire the staple after a compression of tissue is made. It would be desirable to have a precise surgical stapler device that is compact and easy to use and will quickly and easily fire. Also, once compression of the desired stapling location is made, only a very limited degree of force to the surgical stapling device should be required in order to complete the actuation of the device and thus firing of the staples such as by actuating a trigger switch. Moreover, such a powered stapling device should be very easy to manipulate and hold by the surgeon.

Attempts have been made in the art to provide such a surgical stapling device that is pneumatic or gas powered and/or also externally powered in order to remedy this desire. However, it would be beneficial to provide a disposable apparatus for the application of staples to body tissue that is self contained, self powered and easy to manufacture.

SUMMARY

According to a first aspect of the present disclosure, there is provided a surgical stapler. The stapler has a handle assembly including a stationary handle and a trigger. The trigger is configured to manipulate a cam member through an actuating stroke. The stapler has an elongated body extending distally from the handle assembly and defining a longitudinal axis with a staple cartridge supported adjacent the distal end of the elongated body and containing a plurality of staples. The stapler has an anvil pivotally mounted in relation to the cartridge adjacent the distal end of the elongated body. The anvil has a fastener forming surface thereon and is mounted for pivotal movement in relation to the cartridge between an open position having a distal end spaced from the staple cartridge and a closed position in close cooperative alignment with the staple cartridge. The stapler has an actuation sled supported within the cartridge. The actuation sled is movable to urge the plurality of staples from the cartridge. The stapler also has a drive assembly with a body having a working end and a cam member supported on the working end. The cam member is positioned to translate relative to the anvil to maintain the anvil in the closed position during firing of the stapler.

The trigger is operatively connected to a power cell. The power cell is operably connected to a motor of the drive assembly. The manipulation of the trigger actuates the power cell such that the power cell powers the drive assembly to effect translation of the cam member relative to the anvil. The stapler also has a channel for supporting the staple cartridge and the motor of the drive assembly controls the actuation sled supported within the cartridge. The actuation sled urges the plurality of staples from the cartridge when the anvil is in the closed position and in cooperative alignment with the staple cartridge.

According to another aspect of the present disclosure, there is provided a surgical stapler. The stapler has a handle assembly with a stationary handle and a trigger configured to manipulate a cam member through an actuating stroke. The stapler also has an elongated body extending distally from the handle assembly and defining a longitudinal axis. The stapler also has a staple cartridge supported adjacent the distal end of the elongated body and containing a plurality of staples with an anvil pivotally mounted in relation to the cartridge adjacent the distal end of the elongated body. The anvil has a fastener forming surface thereon and is mounted for pivotal movement in relation to the cartridge between an open position having a distal end spaced from the staple cartridge and a closed position in close cooperative alignment with the staple cartridge.

The stapler has an actuation sled supported within the cartridge. The actuation sled moves to urge the plurality of staples from the cartridge. The actuation sled is connected to a drive rack. The drive assembly has a body with a working end and a cam member supported on the working end. The cam member is positioned to translate relative to the anvil to maintain the anvil in the closed position during firing of the stapler.

The trigger is operatively connected to a power cell. The power cell is operably connected to a motor of the drive assembly such that manipulation of the trigger actuates the power cell such that the power cell powers the drive assembly to effect translation of the cam member relative to the anvil. The stapler also has a channel for supporting the staple cartridge. The motor of the drive assembly controls the actuation sled supported within the cartridge. The actuation sled urges the plurality of staples from the cartridge when the anvil is in the closed position and in cooperative alignment with the staple cartridge.

The stapler also has a protective casing. The protecting casing houses the power cell and the motor in the protective casing and is connected to the stationary handle. The motor has a motor drive shaft that extends through the stationary handle to connect with the drive rack.

According to another aspect of the present disclosure, the surgical stapler is powered by an inexpensive disposable power source that may be actuated by a manual or automatic switch or switch system and that has a power cell coupled to a motor assembly to assist with actuation and firing of the staples.

In another embodiment, the stapler has a power supply that can actuate the stapler and the power source can easily move the drive mechanism to an appropriate position for the next stapling operation.

According to another aspect of the present disclosure, there is provided a surgical stapler. The stapler has a handle assembly including a trigger and a clamping device including a staple cartridge with a plurality of staples and an anvil having a fastener forming surface thereon. The stapler also has a controller configured to determine an occurrence of clamping by the anvil and the staple cartridge. The controller controls firing of the plurality of staples from the staple cartridge. When the trigger is actuated the controller delays firing of the plurality of staples from the staple cartridge to provide for a predetermined time period of tissue compression of the tissue between the anvil and staple cartridge. The controller outputs a control signal to allow firing once the predetermined time period is reached. The stapler also has a motor having a geared assembly. The motor is disposed in the handle and configured to receive the control signal from the controller. The motor is operatively connected to the staple cartridge to fire the staples from the staple cartridge once the control signal is received.

DESCRIPTION OF THE DRAWINGS

Other and further objects, advantages and features of the present disclosure will be understood by reference to the following specification in conjunction with the accompanying drawings, in which like reference characters denote like elements of structure and.

DETAILED DESCRIPTION

In the drawings and in the description which follows, the term "proximal", as is traditional, will refer to the end of the apparatus which is closest to the operator, while the term "distal" will refer to the end of the apparatus which is furthest from the operator.

The present disclosure shall be discussed in terms of both conventional and endoscopic procedures and apparatus. However, use herein of terms such as "endoscopic", "endoscopically", and "endoscopic portion", among others, should not be construed to limit the present disclosure to an apparatus for use only in conjunction with an endoscopic tube. To the contrary, it is believed that the apparatus of present disclosure may find use in procedures in these and other uses including but not limited to where access is limited to a small incision such as arthroscopic and/or laparoscopic procedures, or any other conventional medical procedures known in the art.

Figure 1:
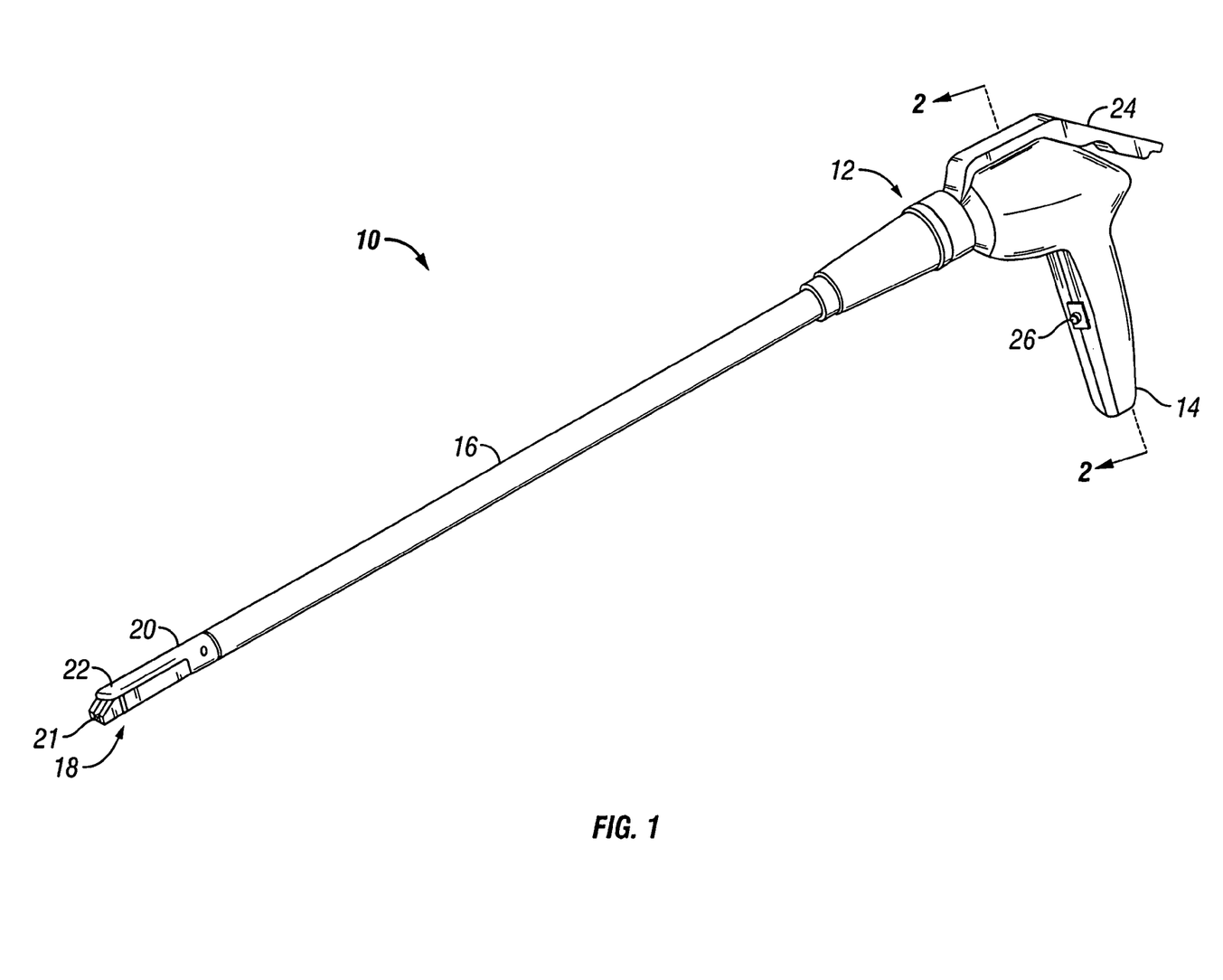
FIG. 1 is a perspective view of a first embodiment of a surgical stapler of the present disclosure.

Referring now to the figures, wherein like reference numerals identify similar structural elements of the subject disclosure, there is illustrated in FIG. 1 a self-contained powered surgical stapler constructed in accordance with one embodiment of the subject disclosure and designated generally by reference numeral 10. The surgical stapler 10 is a disposable surgical instrument. However, the disposable arrangement is non-limiting and other non-disposable arrangements may be contemplated and are within the scope of the present disclosure.

The surgical stapler 10 of the present disclosure shown in a perspective view in FIG. 1 and described herein includes a frame generally represented by reference numeral 12 and handle generally represented by reference numeral 14. The frame 12 defines a series of internal chambers or spaces for supporting various mechanical components of the surgical stapler 10 as well as a number of staples therein for the application to the body tissue.

The frame 12 supports an endoscopic portion 16 or an extended tube-like portion. The endoscopic portion 16 is capable of being rotated and has a relatively narrow diameter, on the order of in a range that includes about 10 millimeters, and is for insertion into a small opening in or tube inserted into the body, such as in the abdominal cavity, or other similar body cavities. The endoscopic portion 16 has a longitudinal axis and has a length. The length is appropriate for reaching the operation site in the interior of the body. The surgical stapler 10 may be used in conjunction with other instruments such as endoscopes or other such optical devices for visually examining the interior of the body, for example, cameras by means of fiber optics or other optical or recording devices.

Generally, the endoscopic portion 16 of the surgical stapler 10 is inserted through the small opening or wound, and is manipulated to the operation site. At the operation site, the surgical stapler 10 is actuated.

The endoscopic portion 16 has a fastening assembly 18 and cutting assembly that is known in the art. The fastening assembly 18 and the cutting assembly are located in a housing 20 which carries a fastener and a cutter to the operation site. The fastening assembly 18 in this one non-limiting embodiment has a pair of jaws 21, 22, or an anvil 22 and a staple cartridge 21. The jaws 21, 1o 22 may be a first jaw 21 and second jaw 22 that opens and closes or alternatively another clamping structure for compression of the tissue at the stapling site. The jaws 21, 22 are defined by a staple carrying cartridge 21 and the anvil 22 that is located therein. The staple carrying cartridge 21 is in one embodiment located at the distal end of the housing 20. The staple carrying cartridge 21 has one or a 15 number of rows of staples. The surgical stapler 10 also has an anvil 22 with a forming surface (not shown) and further includes a knife (not shown) as is well known in the art for accomplishing the surgical stapling.

Generally, actuating the operating portion of the fastening assembly 18 is 20 accomplished via intermediate components disposed on or within the narrow longitudinally extending tubular endoscopic portion 16. In one embodiment, a cylindrical tubular sleeve member surrounds the endoscopic portion 16. The sleeve may be manipulated in a direction with the longitudinal axis of the surgical stapling device. The surgical stapler 10 of the present disclosure has three basic actions or functions.

First, the endoscopic portion 16 is introduced into the human or animal body and is positioned with the jaws 21, 22 aligned at the desired stapling site to receive the target tissue. This may involve rotation of the endoscopic portion 16 relative to the body, either by rotating the surgical stapler 10, as a whole, by rotating simply the endoscopic portion 16 relative to the frame 12 as permitted, or a combination of both actions. Thereafter, the surgical stapler 10 secures the target body tissue between the staple cartridge 21 in the distal portion of the housing 20 and the anvil 22. This is accomplished by a clamping action of the jaws 21, 22 or alternatively by another similar or different clamping member. The jaws 21, 22 are allowed to remain in the closed position for a period of time. The jaws 21, 22 remaining closed for a predetermined period of time allow any excess liquid or fluid in the tissues to drain out of the body tissues prior to actuation of the stapling mechanism. This ensures that the liquid does not rapidly traverse out of the tissues to impede formation of the closed or formed staple and ensures a proper staple formation.

With the target tissue clamped between the anvil 22 and the staple cartridge 21, a camming surface which surrounds the housing 20 and anvil member 22 may be employed to close the jaws 21, 22 of the surgical stapler 10 and clamp the tissue between the anvil 22 and the tissue contacting surface of the staple cartridge 21. The jaws 21, 22 may be clamped by actuating or closing lever 24 that is opposite the jaws 21, 22. Thereafter, the third action of the operator or more particularly the surgeon is that of applying the staples to the body tissue. A longitudinally extending channel is employed to deliver longitudinal motion to an axial drive member and a tissue cutting knife.

The stapler 10 may have an axial drive member or an axial drive screw to contact a pusher. The pusher elements drive the staples through the body tissue against the fastener or forming surface of the anvil 22. Typically, in the art the surgical stapler 10 fires usually by an actuation of a first trigger 26. Thereafter, the clamping action of the jaws 21, 22 is released and the surgical stapler 10 or a portion thereof may be withdrawn from the body cavity or site.

A known and recognized benefit is that often an operator will desire a surgical stapler 10 that is self-actuating or that actuates with only a limited degree of physical force using the trigger handle (not shown) or using a trigger switch 26. It is envisioned that surgeons would desire such a surgical stapler 10 that does not have to be connected to any external power supply but instead includes an internal battery operated power supply. Operators would desire a surgical stapler having an internal power source that is comfortable to hold, compact and that is very suitable for endoscopic or laparoscopic procedures as well as other conventional surgical procedures. The stapler 10 of the present disclosure is advantageous since it is a compact and ergonomic member. It is also very advantageous to form such a surgical stapler 10 from few component parts relative to the prior art surgical instruments. This reduces manufacturing costs of the surgical stapler.

Figure 1A:
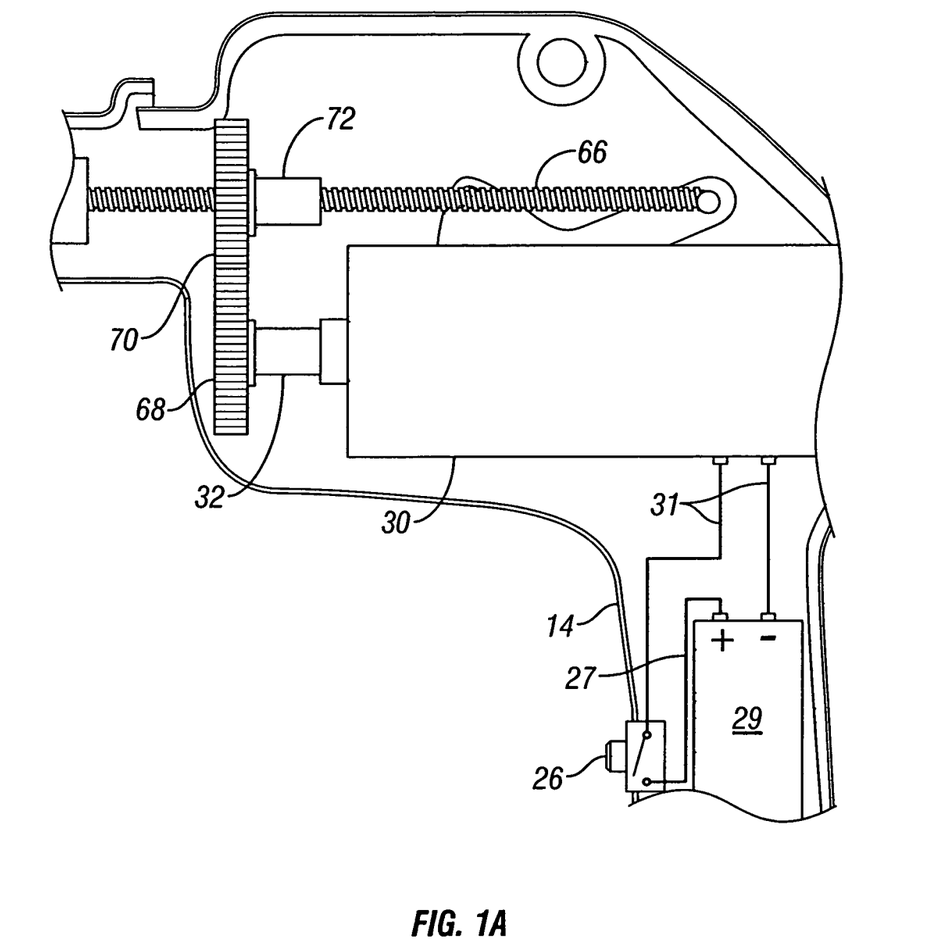
FIG. 1A is a schematic of the handle portion of the surgical stapler of FIG. 1 showing the trigger switch and a power cell coupled to a motor.

The present disclosure in one embodiment uses a motor drive source having a substantially offset or a direct drive to remedy these known issues in the art. FIG. 1A shows a schematic illustration of an interior of the handle 14. The surgical stapler 10 in this embodiment is powered by a motor 30. The trigger switch 26 in this embodiment is connected by lead 27 to a power source 29 such as a battery. The battery 29 is connected by lead 31 to a motor 30. The motor 30 is connected by lead 31 to the switch 26. Upon the actuation of switch 26, power will traverse from the battery 29 to the motor 30. The energized motor 30 will rotate the motor drive shaft 32 to spin gear 68. Gear 68 is in contact with gear 70. Gear 68 rotates second gear 70 which will rotate drive screw 66. The drive screw 66 upon rotation will move in a longitudinal manner to actuate one or more other components of the surgical stapler 10 such for compression of tissue or stapling. Although, the battery 29 and the motor 30 are shown as being located in the handle 14, other locations are contemplated.

Figure 2:
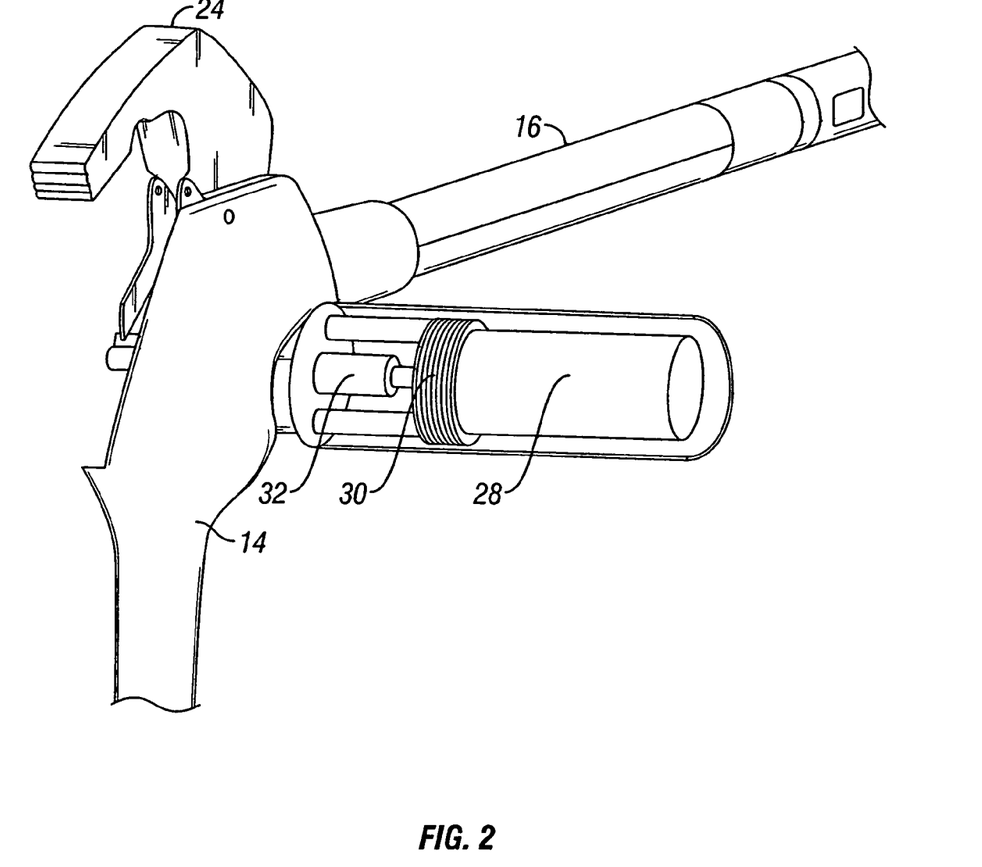
FIG. 2 is an exterior cross sectional view of the surgical stapler along line 2-2 of FIG. 1 with the surgical stapler having a drive compartment thereon.

Referring now to FIG. 2, there is shown a cross sectional view of the surgical stapler 10 of the present disclosure along line 2-2 of FIG. 1 from a rear view of the surgical stapler of FIG. 1. Disposed on an adjacent side of the surgical stapler 10 is shown a protective housing 28. The protective housing 28 is for housing one or more components of the surgical stapler 10. The protective housing 28 may be disposed on either adjacent side of the handle 14 or in another position being parallel with the handle. The protective housing 28 is a generally a cylindrical compact member having an interior that is disposed adjacent to, and on a lateral side of the handle 14. The protective housing 28 is made from a suitable thermoplastic member that is suitable for surgical procedures and has a suitable volume to hold one or more commercially available batteries, or another power source. Although shown as cylindrical, other shapes are possible and the protective housing 28 is not limited to this configuration. The protective housing 28 has the interior space. The space has a compact size and has an advantageous drive source 30 disposed therein.

The surgical stapler 10 of the present disclosure may have a first axial drive shaft for operation of the stapling mechanism in the proximal end of the surgical stapler 10 as is known in the art. Such stapling mechanisms are well known in the art and may be found in U.S. Pat. No. 6,330,965 B1 to Milliman, et al., U.S. Pat. No. 6,250,532 B1 to Green, et al., U.S. Pat. No. 6,241,139 B1 to Milliman, et al., U.S. Pat. No. 6,109,500 to Alli et al., U.S. Pat. No. 6,202,914 B1 to Geiste, et al., U.S. Pat. No. 6,032,849 to Mastri, et al. and U.S. Pat. No. 5,954,259 to Viola, et al., which are all herein incorporated by reference in their entirety.

The drive source 30 has electrical contacts to an integrated power supply and an optional switch system. The drive source 30 is run by any integrated power supply that is compact, and low cost to manufacture. In one embodiment, the drive source 30 also has a suitable amount of torque in order to fire and apply the staple to the body tissue or bone, and form the staple using a forming surface disposed on an anvil. In one embodiment, the drive source 30 is a simple motor assembly having a drive shaft 32. The motor may be any device that converts the current from the portable power cells into mechanical energy but may be any motor that is low cost and that may be disposable and easily discarded after use. The drive shaft 32 is connected through the handle 14 through a sealed aperture in the handle 14. Aperture may be sealed using an "O" ring or similar structure to ensure no fluids enter the stapler 10.

Alternatively, the drive source 30 may comprise any electrically powered motor known in the art. The present disclosure provides that the drive source 30 may have a number of modular components that are disposable, permanent, replaceable or interchangeable. In one aspect, the motor 30 may be a modular component and replaceable. In another aspect, the battery can be a modular component and replaceable separate from the drive source 30. In still another aspect, both the battery and the motor of the drive source 30 may be modular components. The motor and battery may be stored in a casing or be separate units.

In one embodiment, the drive source 30 has electrical contacts to, and is powered by, one more internal power cells. The power cells may be one or more disposable or rechargeable power cells. For example, the power cells may be a nickel cadmium type battery, an alkaline battery, a lithium battery, or a nickel metal hydride and may be replaceable or disposable with the entire surgical stapler 10. Alternatively, the power cells of the drive source 30 may also disengage from the surgical stapler 10 for recharging. Once disconnected, the surgical stapler 10 itself then may be discarded after use.

In one embodiment, the one or more power cells of the drive source 30 are disposed and oriented in a generally perpendicular fashion relative to an outer surface of the handle 14 as shown in the housing 28 and optionally may be located in a casing with the motor assembly. In this non-limiting embodiment, the surgical stapler 10 may have a discrete analog switch assembly to actuate the drive source. The switch assembly may be located in any location or on an external surface of the surgical stapler 10, or be integral with the trigger switch 26. Alternatively, the drive source 30 may be actuated by a counter clockwise rotation of the protective housing 28 to actuate the drive source. Still further in another embodiment, the drive source 30 may be actuated by the trigger 26 or by simply the lowering an elevation of the lever 24.

Figure 3:
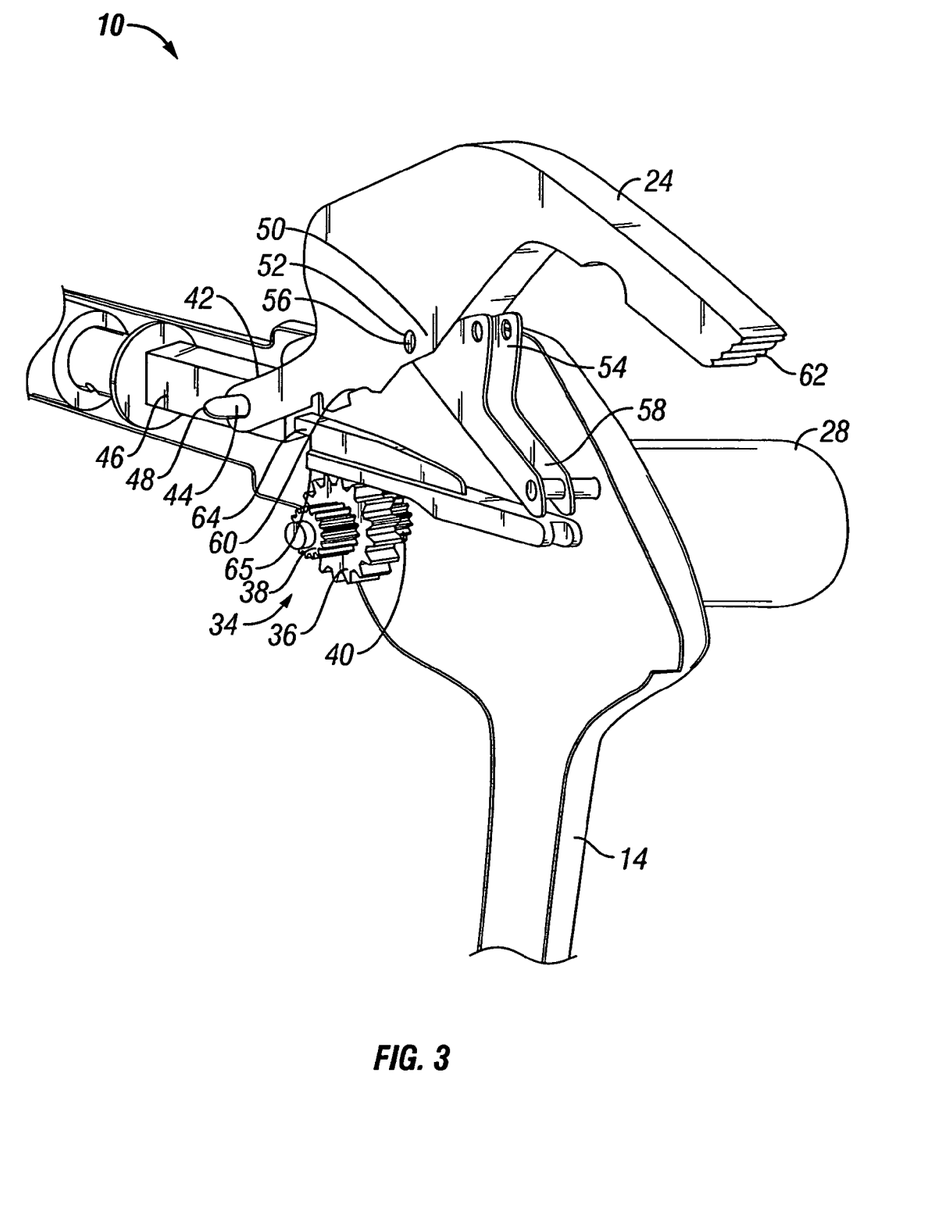
FIG. 3 is an interior cross sectional view of the surgical stapler being opposite the compartment.

Referring now to FIG. 3, there is shown an opposite lateral side cross-sectional view of the surgical stapler 10 of FIG. 2, having the lever 24 in an elevated position or elevated and away from the handle 14. The drive shaft 32 of the drive source 30 extends through the lateral side wall of the handle 14 and engages a gear assembly 34. The gear assembly 34 may have any number of gears to transmit motion from the drive source 30 in protective housing 28 to another member to move a suitable driving member for stapling. The driving member is a gear rack or drive screw or other member to fire the staples in the staple cartridge 21. Various driving configuration are possible and the present stapler 10 is not limited to any such particular driving arrangement. In this one non-limiting embodiment, the gear assembly 34 has a main gear 36 and two subordinate gears 38, 40. The gear assembly 34 laterally extends into the interior space of the handle 14 as shown. In one embodiment, the gear 36 is a spur gear. In one embodiment, the subordinate gears 38, 40 are a pair of pinion gears. In yet another embodiment, instead of a pair of pinion gears 38, 40, the stapler 10 may have one pinion gear. Various gearing configurations are possible and within the scope of the present disclosure.

The lever 24 as shown has a first lever side 42 that has a transverse aperture 44 being disposed therethrough. The lever 24 is connected to a member 46 by a link pin 48 through aperture 44 in the lever 24. The member 46 moves laterally through the endoscopic portion 16. The member 46 controls the jaws 21, 22 shown in FIG. 1 to open or close and for the surgeon to clamp the jaws of the surgical stapler 10 on or at the desired tissue site. The lever 24 also has an intermediate portion 50. The intermediate portion 50 has a second aperture 52 being disposed in a bottom side of the lever 24. The lever 24 is further connected to a second linkage assembly 54 through the second aperture 52 by a second link pin 56. It should be appreciated that the powered arrangement is not limited to any such device that requires tissue approximation such as a TA surgical stapler such as U.S. Pat. No. 6,817,508 to Racenet, et al. which is herein incorporated by reference in its entirety, and the powered arrangement may encompass other staplers that do not require any such tissue approximation prior to firing.

In one embodiment, the second linkage assembly 54 has two discrete links. Each of the links is spaced apart and is connected to one another to form 1o an integral second linkage assembly 54. The second linkage assembly 54 is for translating a downward force from the lever 24 into an axial lateral force and for moving one or more structures in the handle 14. The second linkage assembly 54 is further fixedly connected to an interior pin 58 of the handle 14. The lever 24 still further has an orthogonal notch 60. The notch 60 is disposed on the lever 24 with the notch being between the transverse aperture 44 and the second aperture 52. The notch 60 provides clearance and prevents the lever 24 from interfering or otherwise contacting the gear assembly 34 during a firing sequence or otherwise when the drive source 30 is actuated.

As shown in the raised position, the free end 62 of the lever 24 rests elevated above the handle 14 as shown. As mentioned, when a stapling site is determined by the operator, the operator will use the jaws 21, 22 to compress the tissue at the stapling site to clamp the tissue for a period of time. The surgeon can control the jaws by lowering or closing lever 24 (from the elevated position to a position that rests on the handle 14). Upon lowering the lever 24 from the elevated position above the handle 14, the lever 24 lowers the second linkage assembly 54.

The second linkage assembly 54 forces the lever 24 at the first side 42 to move the member 46. The member 46 is then manipulated in a lateral axial direction opposite the handle 14. Thus, member 46 drives the jaws 21, 22 at the distal side of the surgical stapler 10 for clamping the selected body tissue between the jaws. In one embodiment, the member 46 may further contact a lead, switch or mechanical member in order to provide an audible or visual alert so as to inform the physician/operator that a preset period of time has elapsed for compression of tissue between the jaws and the firing can begin. Various clamp arrangements are possible and the present arrangement is for illustration purposes as it is envisioned that the clamp may be powered by the drive source 30, or by a separate drive source.

In another embodiment of the surgical stapler 10, the surgical stapler 10 may be manually actuated for stapling. In the manual embodiment, when the desired stapling is desired, the operator will actuate either a trigger handle (not shown) or in another embodiment will actuate a handle assembly having a linkage. Still in another embodiment, the lever 24 may operate the switch assembly at an end of the lever 24. The switch assembly 26 may be on any location of the surgical stapler 10 or may be adjacent to the protective housing 28.

The surgical stapler 10 further has a firing member 64. The firing member 64 is laterally disposed in the handle 14 and can optionally assist with driving an axial drive screw or another driving member to actuate the stapling mechanism in the distal side of the surgical stapler 10. The firing member 64 may include a single driving member that can control both the clamping and the firing of the surgical stapler 10. In another embodiment, the firing member 64 can alternatively include separate driving members with one driving member for the firing of the stapler cartridge 21 and another driving member for closing the jaws 21, 22. Various configurations are possible and within the scope of the present disclosure. The firing member 64 is a longitudinal member having a bottom driving surface 65. However, the longitudinal firing member 64 can be a single component or constructed of other multiple members. The firing member 64 is disposed in a longitudinal manner in the interior of the handle 14 of the surgical stapler 10. Upon actuation, the motor in the housing 28 spins the main gear 36 that contacts or is connected to the bottom driving surface 65 of the firing member 64. Gear 36 rotates in a counterclockwise fashion. Thus, in this manner, the drive source 30 will rotate the gear assembly 34 that will move the firing member 64 in an axial direction toward the distal direction of the surgical device 10 and away from the handle 14. A rotation of the main gear 36 applies a force to the firing member 64 on the bottom driving surface 65 for the purpose of axially moving the firing member in a longitudinal distal manner. This axial movement of the firing member 64 will impart an axial force the corresponding member in the endoscopic potion 16 that will engage the stapling mechanism.

A beneficial aspect of the present disclosure is that the drive source 30 will then allow a greater amount of torque to be applied to the driving member 64 relative to a manually actuated apparatus without any motor assembly 30. A significant aspect of the present disclosure is that the drive source or motor 30 is a low cost device that may be discarded. Given that the drive source 30 may be discarded, the drive source or motor 30 may be connected to an optional analog or digital circuit on a controller to drive the firing member 64 with a predetermined amount of torque so that a considerable amount of power is released from the drive source 30 each instance the firing is desired. Moreover, the surgical stapler 10 provides that the firing member 64 is directly driven by the drive source 30, or geared by a number of gears for the purpose of actuating the stapling mechanism without undue force or movement applied to the handle 14 or another trigger handle (not shown) of the surgical stapler 10. This is advantageous since the surgeon can precisely locate the stapler 10 at a site and then fire the stapler 10

Figure 3A:
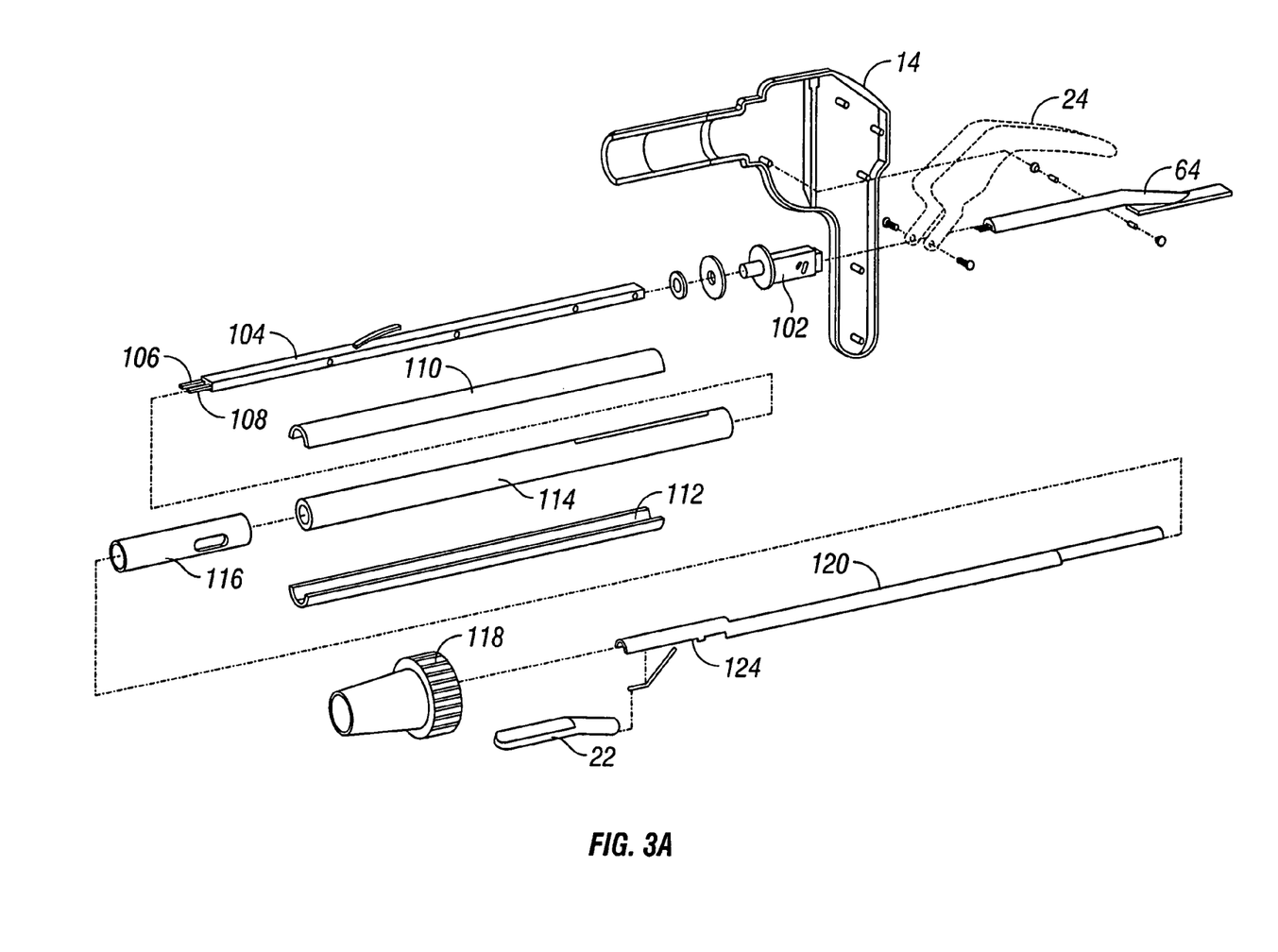
FIG. 3A is an exploded view of a channel of the surgical stapler of one embodiment of the stapler.

FIG. 3A shows an exploded view of a number of components of the surgical stapler 10 of FIG. 1. The stapler 10 has a rack 64 that is slidable in the handle portion 14. The rack 64 interfaces with a clamp tube 102. On a distal side of the clamp tube 102 is a channel 104. The channel 104 engages with the clamp tube 102 and a pair of forks 106,108 on a distal side thereof. The stapler 10 also has an upper cover 110 and a lower cover 112, and an extension tube 114. The extension tube 114 engages with a collar tube 116. The stapler 10 also has a rotation knob 118 with a channel portion 120. The channel portion 120 has a pair of camming surfaces 122 on a distal end. The distal end also has a crimp 124 in a distal side to receive the anvil 22.

In operation, the rack 64 slides and moves the clamp tube 102 distally. The clamp tube 102 is provided to interconnect the handle portion 14 and the extension tube 114. The channel 104 is slidably mounted for reciprocal longitudinal motion. The extension tube 114 provides support for the surgical stapler 10 and has slots that interface with the collar tube 116. The surgical stapler 10 also has a support 120 for longitudinal motion and to operate the stapling mechanism as described in FIG. 2b. The operation of these components is well known and is disclosed in U.S. Pat. No. 5,318,221 to Green, et al., which is herein incorporated by reference in its entirety.

Figure 3B:
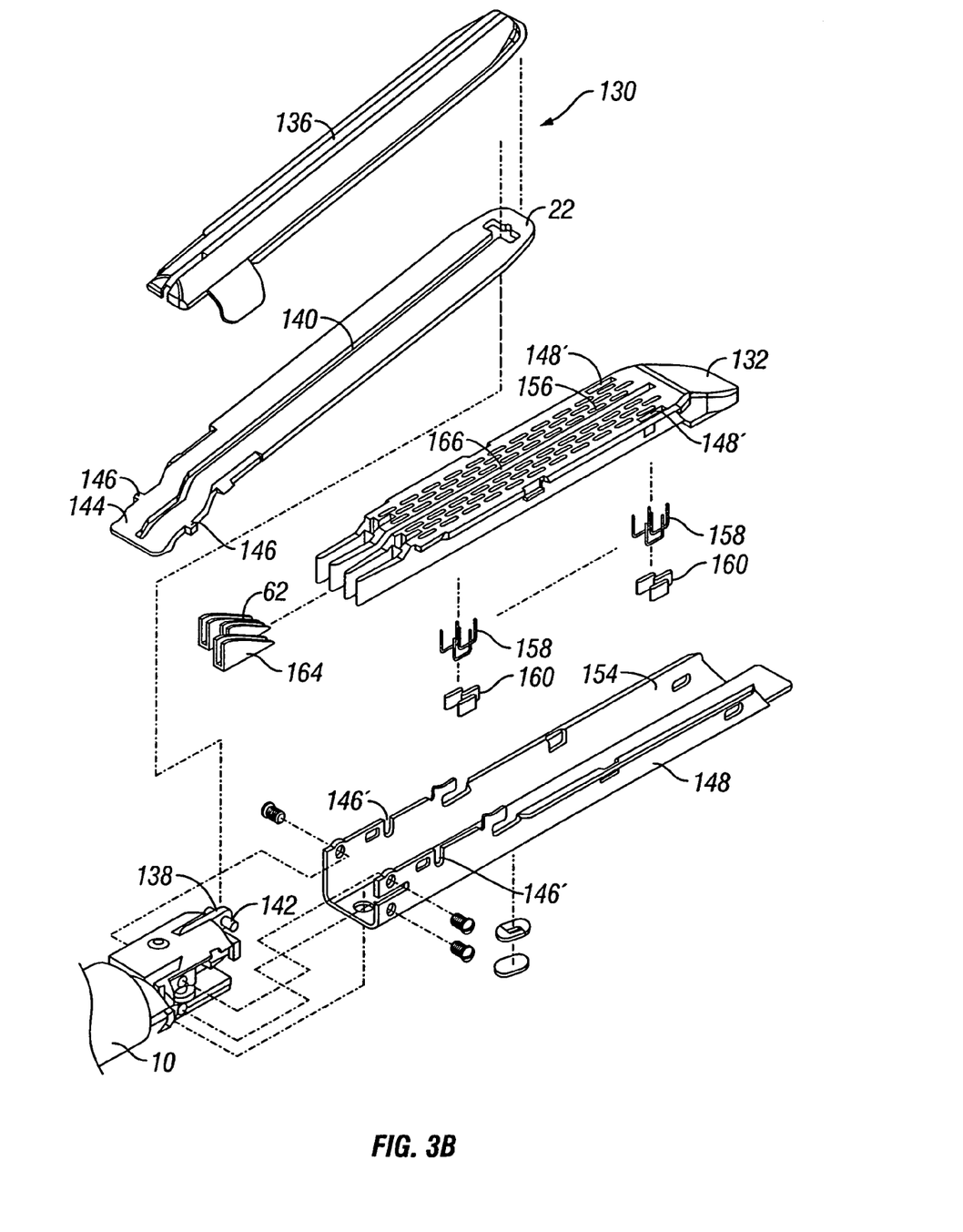
FIG. 3B is an exploded view of the staple cartridge, anvil and the drive sled of FIG. 1.

Advantageously, the rack 64 is driven distally to advance the channel 104 in a distal manner. The channel 104 delivers longitudinal motion to a pusher cam bar or an axial drive member as is known in the art for operation of the staple cartridge 21 shown in FIG. 2b. It should be appreciated that the components shown in FIG. 3A only illustrate one embodiment of the present surgical stapler 10, and instead of the rack 64, the surgical stapler 10 may have a drive screw (FIG. 4) for longitudinal motion and in order to actuate the staple cartridge 21. Referring now to FIG. 3B, there is shown an exploded view of the anvil 22 and the staple cartridge 132 having an actuation sled 169.

Referring to FIG. 2b, the staple cartridge 21 includes an anvil assembly 130 and a cartridge assembly 132 shown in an exploded view for illustration purposes. The anvil assembly 130 includes anvil portion 22 having a plurality of staple deforming concavities (not shown) and a cover plate 136 secured to a top surface of anvil portion 134 to define a cavity (not shown). The cover plate 136 prevents pinching of tissue during clamping and firing of the surgical stapler 10. The cavity is dimensioned to receive a distal end of an axial drive assembly 138.

The anvil 130 has a longitudinal slot 140 that extends through anvil portion 130 to facilitate passage of retention flange 142 of the axial drive assembly 138 into the anvil slot 140. A camming surface 144 formed on anvil portion 22 is positioned to engage axial drive assembly 138 to facilitate clamping of tissue. A pair of pivot members 146 formed on anvil portion 130 is positioned within slots 146' formed in carrier 148 to guide the anvil portion 130 between the open and clamped positions.

The stapler 10 has a pair of stabilizing members 152 engage a respective shoulder formed on carrier 148 to prevent anvil portion 130 from sliding axially relative to staple cartridge 132 as camming surface of the anvil 130 is deformed. Cartridge assembly 132 includes the carrier 148 which defines an elongated support channel 154. Elongated support channel 154 is dimensioned and configured to receive the staple cartridge 132 which is shown above the carrier 148 in the exploded view of FIG. 2b. Corresponding tabs and slots formed along staple cartridge 132 and elongated support channel 148' function to retain staple cartridge 132 within support channel 154 of carrier 148. A pair of support struts formed on the staple cartridge 132 are positioned to rest on side walls of carrier 148 to further stabilize staple cartridge 132 within support channel 154, however other arrangements to support the cartridge 132 on the channel 154 can be used and this arrangement is not limiting.

Staple cartridge 132 includes retention slots 156 for receiving a plurality of fasteners 158 and pushers 160. Longitudinal slots 156 extend through staple cartridge 132 to accommodate upstanding cam wedges 162 of the actuation sled 164. A central longitudinal slot 166 extends along the length of staple cartridge 132 to facilitate passage of a knife blade (not shown). During operation of surgical stapler 10, actuation sled 164 is drive distally to translate through longitudinal slot 156 of staple cartridge 132 and to advance cam wedges 162 distally and into sequential contact with pushers 160, to cause pushers 160 to translate vertically within slots 156 and urge fasteners 158 from slots 156 into the staple deforming cavities of anvil assembly 130 to effect the stapling of tissue.

Figure 4:
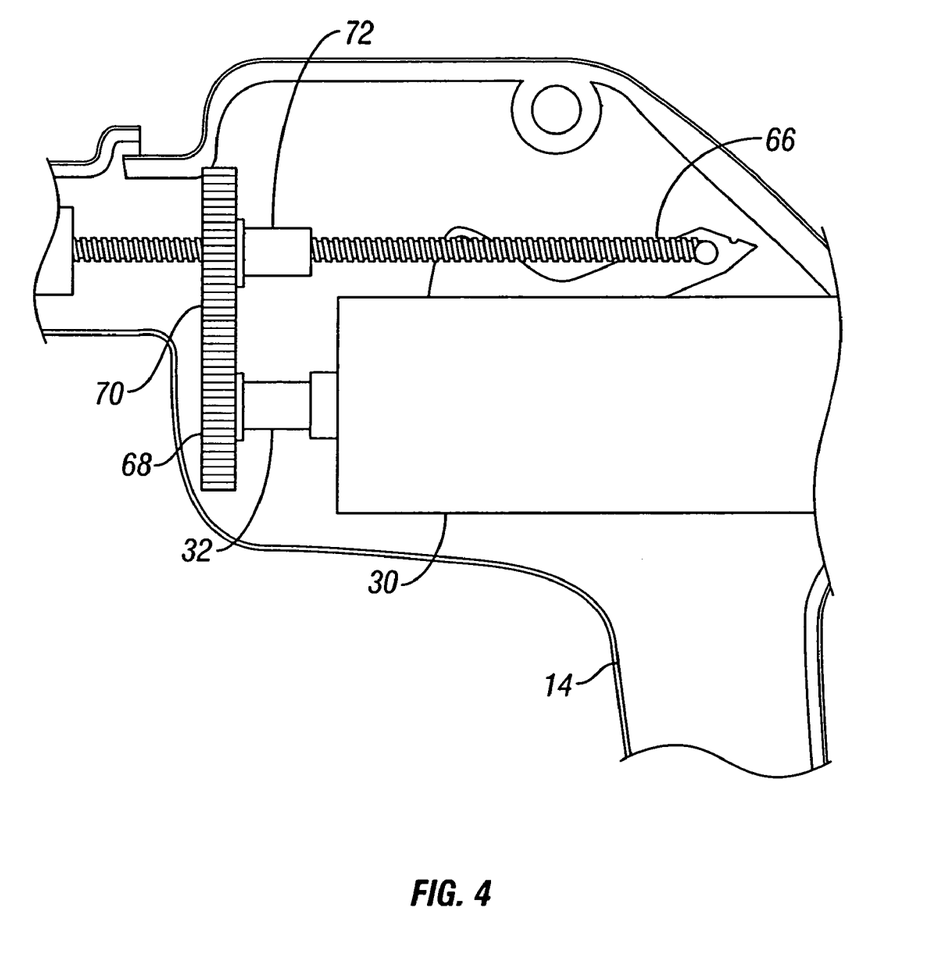
FIG. 4 is another cross sectional view of another embodiment of the surgical stapler of FIG. 1 having a drive source in the handle of the surgical stapler.

Referring now to FIG. 4, there is shown another embodiment of the present disclosure. In this embodiment, the drive source 30 is disposed in an interior space of the handle 14 in a location to balance an overall weight of the surgical stapler 10 for a more ergonomic, comfortable design. The surgical stapler 10, in this embodiment, has a drive screw 66 as a drive member in contrast to the rack 64 of FIG. 3A. The drive screw 66 is a threaded rod having a number of helical grooves that are intended to rotate and contact another axial member shown above to actuate the stapling mechanism in the distal location of the surgical stapler 10 once a tissue compression is made by the surgeon. Various configurations are possible, and it should be appreciated that the stapler 10 of the present disclosure is not intended to be limited to any specific stapler mechanism.

In one embodiment, the drive source 30 is disposed and lies in a longitudinal plane in the handle 14. The drive source 30 is disposed substantially parallel to a longitudinal axis of the surgical stapler 10. This location of the drive source 30 provides for a compact and self powered surgical stapler 10 that may be comfortably balanced and ergonomically grasped by the surgeon. The drive source 30 has the drive shaft 32. Drive shaft 32 is connected to a first drive gear 68. The first drive gear 68 has teeth that mesh with, and rotate a number of teeth of a second translating gear 70 as shown.

The second translating gear 70 further has a bore or aperture in a center of the second translating gear 70. The second translating gear 70 further is connected to a collar 72 in a center of the second translating gear. The collar 72 engages the drive screw 66 of the surgical stapler 10. A clockwise rotation of the second translating gear 70 will also rotate the collar 72 in a similar direction. The collar 72 will then, upon rotation, cooperates and engage with the drive screw 66 to move the drive screw 66 in a distal manner.

This rotation of the collar 72 allows the drive screw 66 to rotate and move distally. The drive screw 66 rotates and moves in an axial manner through the bore of the second translating gear 70 and the collar in a direction toward and through the endoscopic portion 16 of the surgical stapler 10. Upon rotation, the drive screw 66 will traverse laterally by rotation into the endoscopic portion 16 a predetermined amount in a direction away from the handle 14 of the surgical stapler 10 to actuate the stapler mechanism. A significant aspect of this embodiment is that the drive screw 66 has a considerable amount of torque from motor 30 in order to translate the force to the staple mechanism and to form the staples against anvil.

Figure 4A:
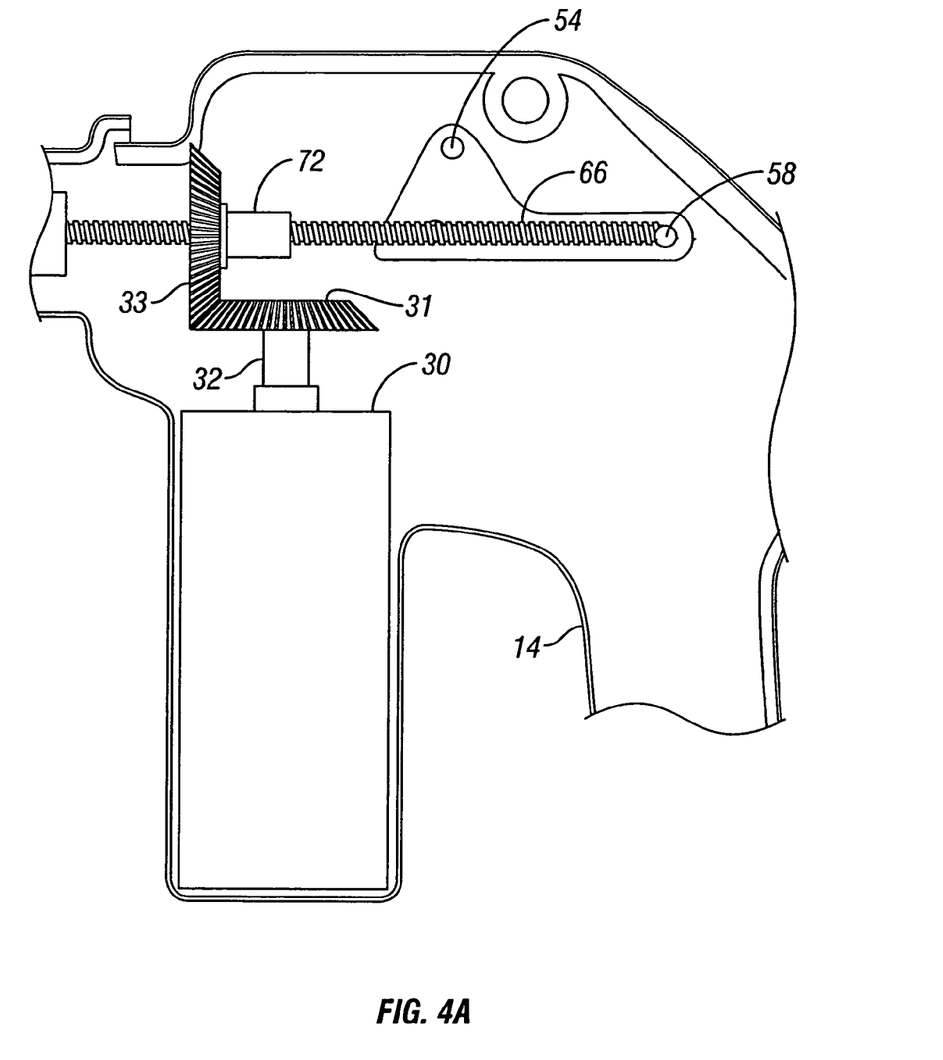
FIG. 4A illustrates another cross sectional view of the surgical stapler of FIG. 1 having a bevel geared arrangement.

FIG. 4A illustrates another embodiment of the surgical stapler 10. In this embodiment, the motor 30 is shown unconnected from any power supply for illustration purposes. The motor 30 has a drive shaft 32. The drive shaft 32 is connected to a first bevel gear 31.

In this embodiment, the motor 30 is disposed at ninety degrees from the drive screw 66. Upon the actuation of trigger switch 26 (FIG. 1) power will traverse from the battery 29 to the motor 30 (FIG. 1A). The energized motor 30 will rotate the motor drive shaft 32 to spin bevel gear 31. Bevel gear 31 is in contact with second gear 33 that is disposed in concentric fashion with drive screw 66 using member 72 as discussed above.

Bevel gear 31 will rotate drive screw 66 to move the drive screw 66 in a longitudinal manner to actuate one or more other components of the surgical stapler 10 such for tissue compression or for stapling. Bevel gear 31 is useful to change a rotation direction of the motor output shaft 32 to move drive screw 66 longitudinally or distally and proximally, and to orient the motor 30 in an advantageous manner relative to the handle 14. Bevel gear 31 has teeth that can be straight, spiral or hypoid. Although bevel gear 31 is shown as perpendicular to gear 33, other arrangements are contemplated. Instead, of bevel gear 31 with second gear 33 oriented as shown the surgical stapler 10 may incorporate a hypoid gear which can engage with the axes in different planes. Hypoid gear may further permit different spacing arrangements of the motor 30 relative to the drive screw 66 to further provide for a more compact, balanced and ergonomic stapler design.

Figure 5:
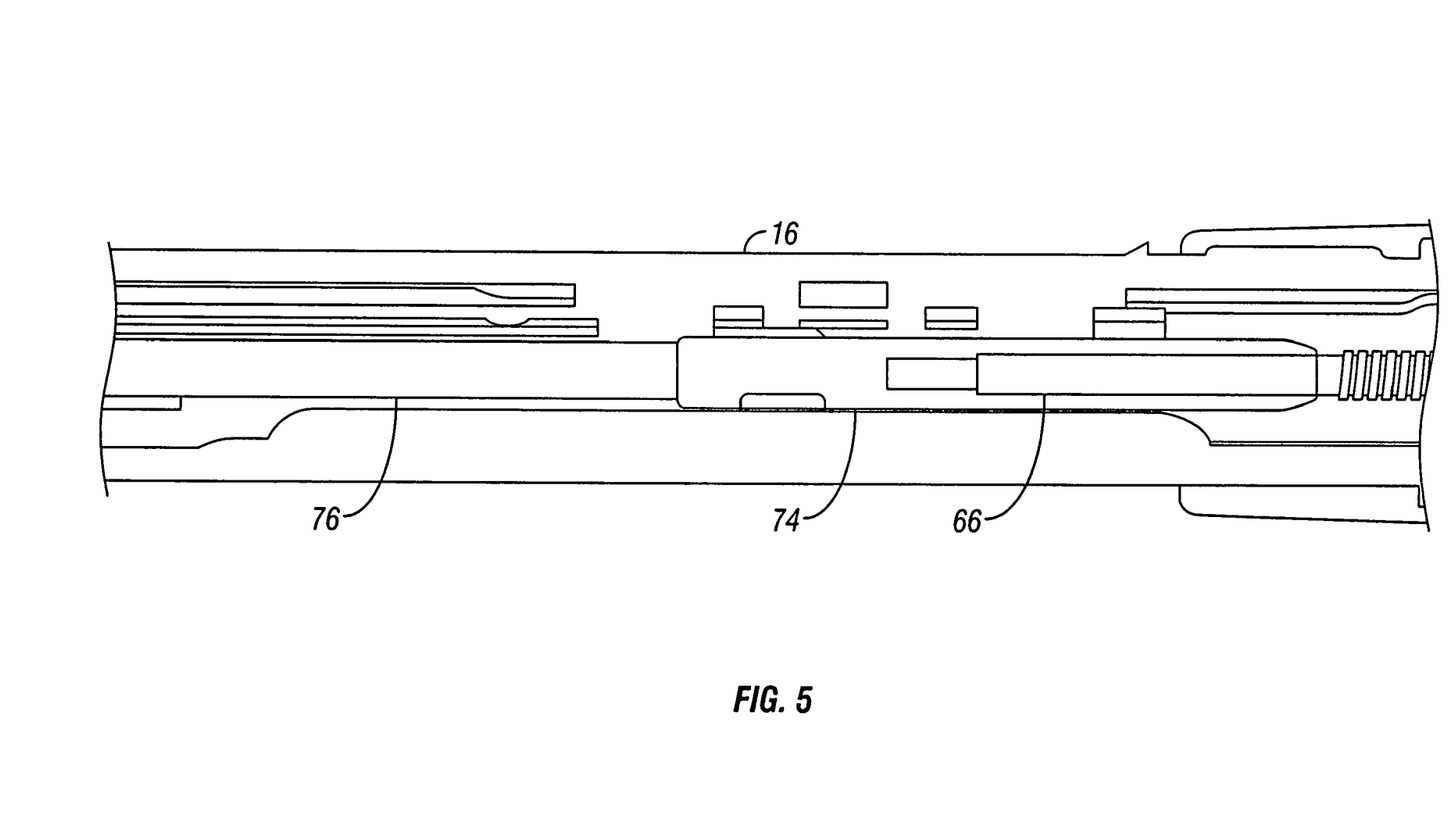
FIG. 5 is a cross sectional view of an endoscopic portion of the surgical stapler of FIG. 4.

Referring now to FIG. 5, there is shown a cross sectional view of the endoscopic device 16. Upon actuation, the drive screw 66 rotates a predetermined distance through a central bore 74 in the endoscopic portion 16. After traversing the predetermined distance, the drive screw 66 will contact a longitudinal firing member 76. The longitudinal firing member 76 will then contact a complementary structure to fire the staples in the staple cartridge 21 in the distal region of the surgical stapler 10 as is known in the art. In another exemplary embodiment, of the present disclosure, the drive source 30 may be a reversible drive source. Additionally, the staple cartridge 21 may have one row or multiple rows of staples and the surgical stapler 10 may fire with an amount of torque to easily form staples having the desired configuration.

In this alternative embodiment, the drive screw 66 may reverse automatically or manually to move proximally at the conclusion of the stapling relative to the endoscopic portion 16. Upon the drive source 30 actuated by the switch 26 or another manual or automatic actuating device, the drive source rotates the drive shaft 32 in the opposite rotational direction. The drive shaft 32 then rotates the first drive gear 68 in the opposite rotational direction. Thereafter, a number of teeth of the first drive gear 66 rotate the second translating gear 70 in the opposite direction. The second translating gear 70 will then rotate the drive screw 66 in the opposite direction to return the drive screw 68 to an initial position for the next stapling operation.

Figure 6:
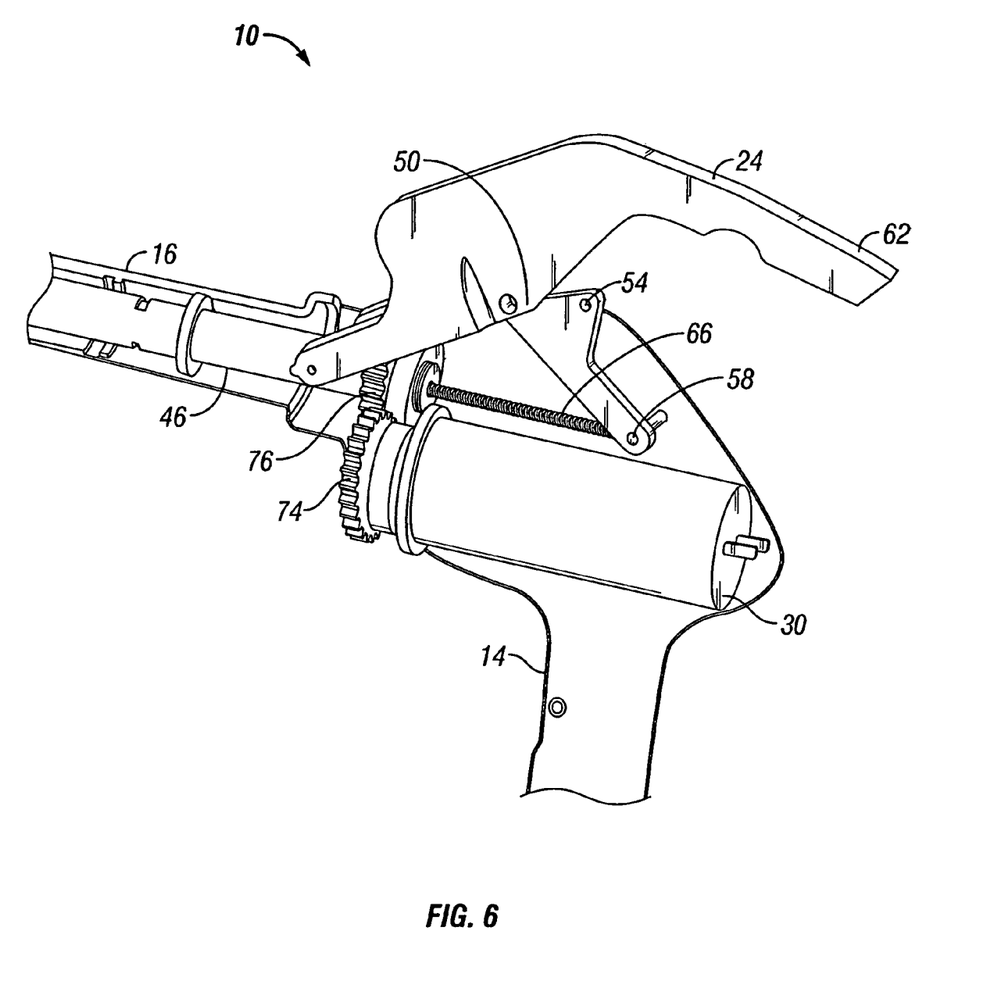
FIG. 6 is yet another cross sectional view of another embodiment of the surgical stapler of FIG. 1 with the drive source being in the handle and geared to the drive screw of the surgical stapler.

Referring now to FIG. 6, there is shown another alternative embodiment of the present disclosure. In this embodiment, the jaws 21, 22 are powered by the drive source 30. The jaws 21, 22 may be moved in close alignment with one another to clamp tissue therebetween and be powered by motor or drive source 30. The surgical stapler 10 has a drive source 30 that has a drive gear 74 being connected to the output drive shaft (not shown) of the motor 30 or drive source. The drive gear 74 is directly connected to the drive source 30, however alternatively may be connected to the drive source 30 by another gear or by another linkage depending on the space constraints of the handle 14. The surgical stapler 10 further has a second translation gear 76. The second translation gear 76 also is connected through the drive screw 66 that drives the drive screw 66 to fire the staple cartridge 21 as discussed previously.

In this embodiment, the lever 24 is connected to the linkage assembly 54 at the intermediate portion 50 of the lever 24. The lever 24 when lowered from the elevated position, imparts a downward force on the linkage assembly 54. Thereafter, the linkage assembly 54 fixed at one end by the interior pin 58 rotates about the interior pin and moves the lever 24 in an axial manner. This moves and advances a linkage (not shown) for clamping the tissue. Still further, the member or another component may actuate a timer (not shown) or display to alert the physician/operator to activate the trigger and to initiate the drive source 30. In still another embodiment of the present disclosure, the clamping may be mechanically connected or linked to the drive source 30 to provide for a powered compression of tissue. In still another embodiment, the clamping can be performed simultaneously with the firing of the trigger handle 26, and may be powered by the drive source 30 as opposed to independently of firing.

Once the actuation of the drive source 30 occurs, the drive source will turn the drive gear 74. The drive gear 74 will then directly rotate the second translation gear 76 and the drive screw 66 disposed directly through the bore of the second translation gear. Again, the drive screw 66 will then impart the required axial force to discharge the staples from the staple cartridge 21 in the distal location of the surgical stapler 10. As mentioned, once the drive screw 66 travels a predetermined distance, the drive screw 66 will actuate the corresponding stapler mechanism to fire the staples in the staple cartridge 21.

Although shown as an endoscopic surgical stapler, the present drive system may be used with any surgical stapling device known in the art, such as endoscopic surgical stapling devices, a multi-fire GIA surgical stapler, a TA surgical stapling device, and/or any other surgical stapler device known in the art. The present instrument may also be used with a single drive surgical stapler that drives both the clamping device of the jaws 21, 22 and the stapling device.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical stapler comprising:
   a handle assembly including a trigger;
   a clamping device having a staple cartridge containing a plurality of staples and an anvil having a fastener forming surface thereon;
   a controller configured to determine an occurrence of clamping by the anvil and the staple cartridge, the controller controlling firing of the plurality of staples from the staple cartridge;
   wherein when the trigger is actuated the controller delays firing of the plurality of staples from the staple cartridge to provide for a predetermined time period of tissue compression between the anvil and the staple cartridge and wherein the controller outputs a control signal to allow firing once the predetermined time period is reached; and
   a motor having a drive assembly, wherein the motor is operably associated with the handle assembly and configured to receive the control signal from the controller, the motor being operatively connected to the staple cartridge to fire the staples from the staple cartridge once the control signal is received.

2. The surgical stapler of claim 1, wherein the motor is connected to a power cell selected from the group consisting of an alkaline battery, a nickel cadmium battery, a lithium battery a nickel metal hydride battery, and any combination thereof.

3. The surgical stapler of claim 2 wherein at least one of the motor and the power cell are located in a protective housing.

4. The surgical stapler of claim 1 wherein the anvil is pivotally mounted in relation to the cartridge adjacent a distal end of an elongated body, the anvil being mounted for pivotal movement in relation to the cartridge between an open position having a distal end spaced from the staple cartridge and a closed position in close cooperative alignment with the staple cartridge.

5. The surgical stapler of claim 1 further comprising an actuation sled, the actuation sled being movable to urge the plurality of staples from the cartridge.

6. The surgical stapler of claim 1 wherein the drive assembly further includes a body having a working end and a cam member supported on the working end, the cam member being positioned to translate relative to the anvil to maintain the anvil in the closed position during firing of the stapler.

7. The surgical stapler of claim 1 wherein the drive assembly of the motor comprises a first gear and a second gear, wherein upon actuation the motor drives the controller to spin the first gear, the first gear being in contact with the second gear, the second gear being operatively connected to an actuation sled, such that the first gear rotates the second gear, the second gear moving the actuation sled distally to urge the plurality of staples from the cartridge.

8. The surgical stapler of claim 7 wherein the second gear and the actuation sled are coupled by a drive screw.

9. The surgical stapler of claim 7, wherein the motor automatically rotates the first gear in an opposite direction after the plurality of staples is urged from the staple cartridge.

10. The surgical stapler of claim 1 wherein actuation of the controller operates the motor and rotates a first gear, the first gear operably coupled to an actuation sled, such that rotation of the first gear causes distal translation of the actuation sled and urges the plurality of staples from the cartridge.

11. The surgical stapler of claim 10, wherein the motor is reversible and rotates the first gear in an opposite direction and causes proximal translation of the actuation sled.

* * * * *